United States Patent [19]

Leroy

[11] Patent Number: 4,480,516
[45] Date of Patent: Nov. 6, 1984

[54] MACHINE FOR CONTINUOUSLY CUTTING A STRIP FOR FORMING SECTIONS WITH ROUNDED EDGES HAVING OPPOSITE CURVATURES

[75] Inventor: Louis Leroy, Creteil, France

[73] Assignee: Etablissements Ruby, Voiron, France

[21] Appl. No.: 322,433

[22] Filed: Nov. 18, 1981

[30] Foreign Application Priority Data

Nov. 19, 1980 [FR] France ............................. 80 24539

[51] Int. Cl.³ .............................................. B26D 7/06
[52] U.S. Cl. ........................................ 83/98; 83/110; 83/152; 83/303; 83/436
[58] Field of Search .............. 83/98, 99, 100, 110, 83/300, 303, 331, 341, 347, 121, 348, 152, 154, 156, 436

[56] References Cited

U.S. PATENT DOCUMENTS

| | | | |
|---|---|---|---|
| 1,310,923 | 7/1919 | Novick | 83/154 |
| 1,738,354 | 12/1979 | Cannard | 83/152 |
| 2,311,692 | 2/1943 | Potdevin | 83/303 |
| 2,499,570 | 3/1950 | Crafts | 83/110 |
| 3,008,709 | 11/1961 | Buslik | 271/10 |
| 3,106,121 | 10/1963 | Novick | 83/346 |
| 3,174,428 | 3/1965 | Huck | 83/152 |
| 3,201,295 | 8/1965 | Dewoskin | 53/429 |
| 3,242,783 | 3/1966 | Schmermund | 83/152 |
| 3,279,290 | 10/1966 | Stemmler | 83/300 |
| 3,338,575 | 8/1967 | Nystrand et al. | 270/59 |
| 3,548,696 | 12/1970 | Hornung | 83/100 |
| 3,611,855 | 10/1971 | Thousand, Jr. | 83/100 |
| 3,698,272 | 10/1972 | Kesten et al. | 83/99 |
| 3,847,046 | 11/1974 | Schmermund | 83/152 |
| 3,948,126 | 4/1976 | Wolfberg et al. | 83/303 |
| 3,998,116 | 12/1976 | Helm | 83/100 |
| 4,036,087 | 7/1977 | Braun | 83/110 |
| 4,149,484 | 4/1979 | Koch | 83/152 |
| 4,157,719 | 6/1979 | Dewoskin | 128/291 |
| 4,202,230 | 5/1980 | Obinata | 83/345 |
| 4,315,794 | 2/1982 | Palmieri | 83/100 |

FOREIGN PATENT DOCUMENTS 2757714 6/1979 Fed. Rep. of Germany ........ 83/110
2400887 3/1979 France .

Primary Examiner—Frank T. Yost
Assistant Examiner—Hien H. Phan
Attorney, Agent, or Firm—N. Jerome Rudy

[57] ABSTRACT

A machine for cutting round-ended sanitary towels from a continuous strip has first and second spaced rotary cutting means with first conveying means for advancing the cut portion from the first rotary cutting means more rapidly than the strip is advanced to the first rotary cutting means, and second conveying means for removing the cut portion from the off-cut which occurs as wastage between two adjacent convex rounded ends of two successive sanitary towels. To remove the off-cut from the second rotary cutting means without risk of losing it in the machine and causing a breakdown, the second rotary cutting means includes a rotary cutter and a rotary counter roll, with suction means incorporated in the counter roll for attracting the off-cut onto the counter roll, even after it has been cut from both the pre-cut arriving from the first rotary cutter and the finished towel entrained by the second conveying means.

15 Claims, 8 Drawing Figures

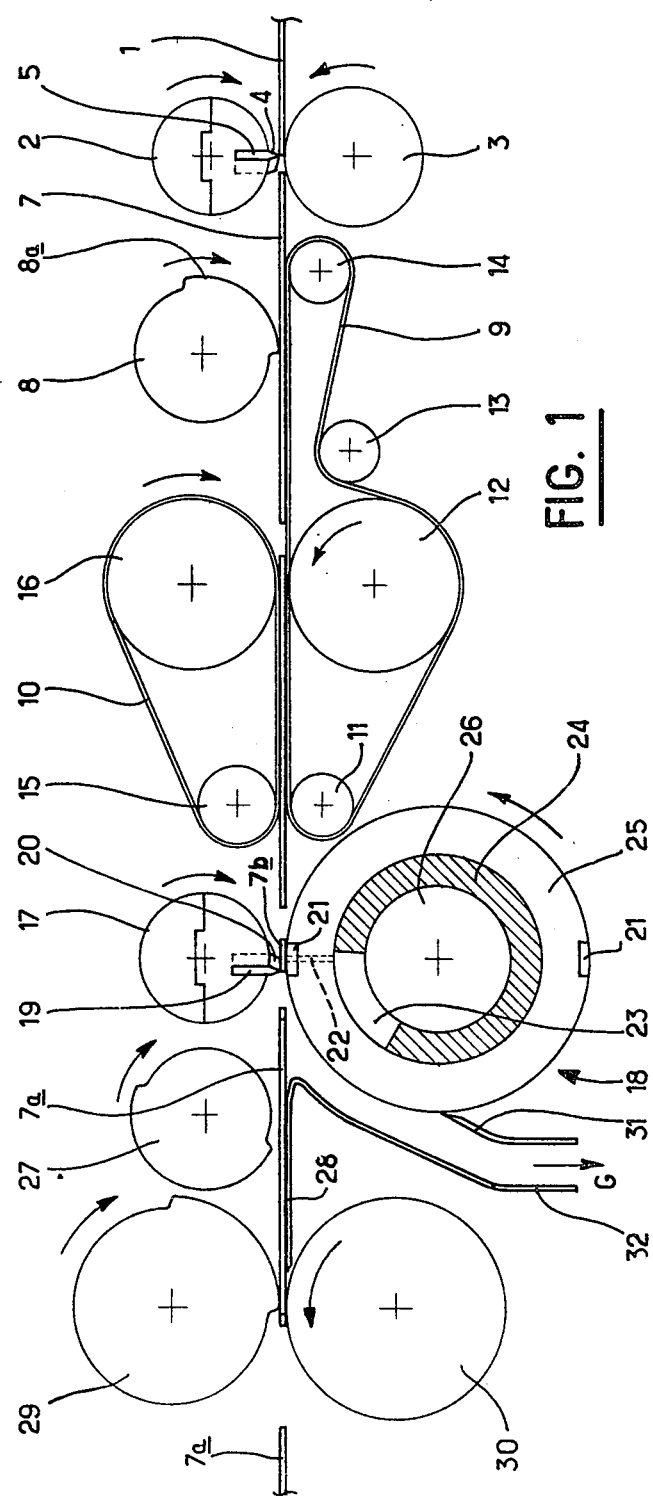
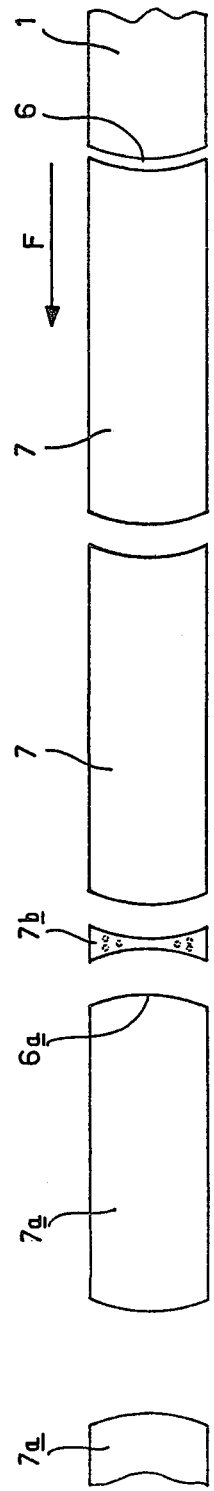
FIG. 1
FIG. 2

MACHINE FOR CONTINUOUSLY CUTTING A STRIP FOR FORMING SECTIONS WITH ROUNDED EDGES HAVING OPPOSITE CURVATURES

FIELD OF THE INVENTION

The present invention relates to a cutting machine intended for continuously cutting sections from a strip which is movable in translation, the cut edges of the sections being rounded and having opposite curvatures. Such a machine is particularly useful for making sanitary towels with rounded ends. Of course, sanitary towels of the type here contemplated are also known as and quite commonly referred to as "sanitary napkins", particularly "feminine sanitary napkins". They are, as is well known, frequently made up of a number of arranged and purposively, for maximized functional effect and capability, of a number of combined and almost invariably adjacently contiguous layers of textile materials or fiber products and/or plastic sheets in any given particular involved structure of same. As such, they may conveniently and accurately described (whether or not referred to as sanitary towels or napkins and so forth) as a stacking, as it were, of (combined) fibrous sheets or fibrous sheets inter-arranged with plastic sheets or films, or both. It is to be understood that the reference to "rounded ends" should be interpreted broadly so that it is not to limit the invention to the formation of cut sections based on an arc of a circle.

BACKGROUND OF THE INVENTION

It is known that sanitary towels for feminine hygiene are made from a continuous strip which is cut into sections having the desired length. The strip is formed from a multiplicity of layers of fibrous or textile products and/or superimposed plastic sheets which are continuously joined. Hitherto, the cutting of the strips has been effected along rectilinear lines of cut perpendicular to the strip axis. It follows from this that the sanitary towels have at their ends rectangular corners which were found to be uncomfortable for the user. It has therefore been contemplated to make sanitary towels with rounded ends. But when this the cutting of the strip generates an off-cut is done which is practically impossible to remove with presently known cutting systems. Thus, the cutting system joins up and, as a result, a manufacturing breakdown occurs.

BRIEF SUMMARY OF THE INVENTION

It is therefore an object of the present invention to provide a new machine for cutting up a strip, moved in translation, into sections having rounded cut edges with opposite curvatures. In the case of making sanitary towels, the convexity of the edges of cut is directed outwardly of the ends of the towel, and the off-cuts have a bi-concave shape. However, the principle of the machine according to the invention may be applied in case it is desired to have a reverse cut where the off-cuts are bi-convex. It must be understood that the use of the machine according to the invention is not limited to the making of sanitary towels. The instant machine can be used whenever it is desired to cut a strip, moved in translation on a continuous basis, to form cut sections with rounded ends, i.e. with either two opposite convex ends or two opposite concave ends.

Accordingly, the present invention provides a machine for cutting a continuous strip which is movable in horizontal translation, to form from the strip cut sections bounded by rounded cut edges with opposite convexities. The present machine comprises, in sequence, along the direction of translation of the strip:

(a) first rotary cutter means including (i) a first cylindrical cutter carrier (ii) a first cutter at the surface of said first cutter carrier, said first cutter having an edge which has a rounded outline, (iii) a first counter roller rotatable to be tangential to the said cutter edge, (iv) an arbor to said first cylindrical cutter carrier, (v) an arbor to said first counter roller, said arbors being fixed in position, parallel and arranged one above the other, and (vi) means rotating said arbors in opposite directions to give the cutter edge and the counter roller a linear displacement velocity equal to that of the strip;

(b) first conveyor means operative to convey a strip section cut by said first rotary cutter means to impart a higher linear velocity than that of the strip when the cut has been effected;

(c) second rotary cutter means including (i) a second cylindrical cutter carrier, (ii) a second cutter carried peripherally by said second carrier, (iii) a second counter roller, (iv) an arbor to said second cylindrical cutter carrier, (v) an arbor to said second counter roller, (vi) means effective to rotate said arbors in opposite directions to give the second cutter and the second counter roller a linear displacement velocity equal to that of the strip section being cut by said second rotary cutter means, said second cutter forming an edge with a rounded outline whose convexity is, at the moment of cut, opposite to that of said first cutter of the first rotary cutter means, said arbors of the second cylindrical cutter carrier and of the second counter roller being fixed in position, parallel and arranged one above the other, the second counter roller being tangential to the cutting edge of said second cutter, and (vii) suction means to said second counter roller effective to apply suction just ahead of the said cutter edge where said second cutter is tangent to said second counter roller, to keep the off-cut on the second counter roller, said suction means being arranged to cut off the application of suction after rotation of the counter roller and off-cut through a fraction of a revolution to allow the said off-cut to be removed from said second counter roller; and (d) second conveyor means imparting a linear velocity to the cut section leaving said second rotary cutting means higher than that of the cut section arriving at said second rotary cutting means.

In a preferred embodiment, the second counter roller comprises: (a) a fixed internal suction chamber constituting a sector of an annulus which subtends with an angle $\theta$ at the center of said second counter roller, the outer wall of the said second counter roller being formed by a sleeve which turns around the above-mentioned annulus, and (b) suction conduits passing through the said sleeve in the zones which come to be just ahead of the edge of the second cutter where the said edge comes to be tangent to the outer surface of the sleeve at the instant of cutting. Opposite the second counter roller, in a zone displaced from the zone of the second cut by an angular rotation greater than $\theta$ around the axis of the second counter roller, there is disposed a recovery chute for the off-cuts. The recovery of the off-cuts in the chute is effected by means of gravity of may be promoted by scraper means bearing on the outer wall of the second counter roller and/or by suction means detaching the off-cuts. The cutter of each said cylindrical cutter carrier is a component inserted in the cylinder of the said carriers. This arrangement is advantageously used for the two cutter means of the machine and the cutter may be set, by means of a wedge, in an inserted component which is integrated in the respective said cylindrical cutter carrier. The outer diameter of the sleeve of the second counter roller may be twice the diameter of the cylindrical surface swept by the cutting end edge of the second cutter. The said swept surface has as its axis the axis of the cylindrical cutter carrier of the second cutter means with the above-mentioned sleeve then carrying in its two cutting zones attached plates comprising at least a part of the suction conduits.

Provision may advantageously be made for the said cylindrical cutter carriers to bear, by means of cylindrical bearing flanges, on their respective counter rollers and to roll on them without sliding. Resilient means are also provided for maintaining the contact of the said cylinders on the said rollers. Moreover, the said second cylindrical cutter carrier may comprise blowing conduits which open out ahead of the edge opposite the zone wherein the off-cut is formed.

It is preferable for each of said first and second conveyor means to comprise at least one rotating cam which bears on the cut section which is the portion that has been subjected to cutting to increase its linear velocity. The said cut section is carried by counter surface means. In a first variant, which may for instance be used for the first conveyor means, the counter surface means is a belt driven at the linear velocity which one wishes to impart to the cut section. In a second variant, which may for instance be used for a first accelerating cam of the second conveyor means, the counter surface means is a fixed plate along which the carried cut section slides. In a third variant, which may be used for instance for a second accelerating cam of the second conveyor means, the counter surface means is a roller driven at the linear velocity of the surface of the cam with which it cooperates.

The machine in accordance with the invention may advantageously be used for cutting a strip formed by a multiplicity of layers of fibrous or textile products and/or plastic sheets. The cut sections, may desirably form sanitary towels.

BRIEF DESCRIPTION OF THE DRAWINGS

In order that the present invention may more readily be understood, there will now be described an embodiment represented in the attached drawing by way of a purely illustrative and non-restrictive example. In these drawings:

FIG. 1 is a schematic elevation showing the elements of a cutting machine, according to the invention, which may be used for cutting sanitary towels with rounded ends;

FIG. 2 is a plan view representing the succession of the cut sanitary towel sections illustrated in side view in FIG. 1, the sections of FIG. 2 being directly below the corresponding sections represented in outline in FIG. 1;

DETAILED DESCRIPTION OF THE PREFERRED EMBODIMENT

Figure 3:
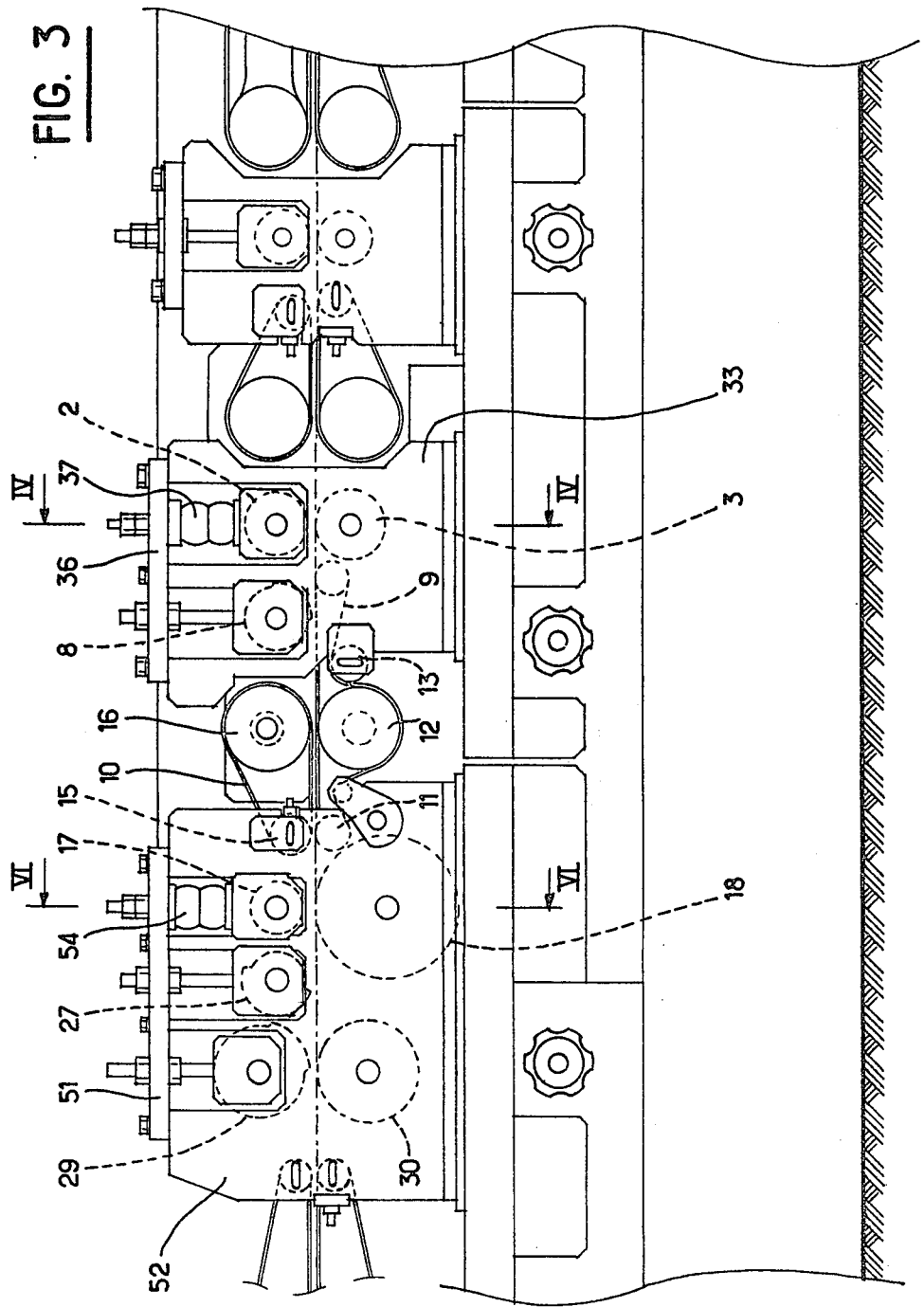
FIG. 3 is an elevation, in more detail, of the part of the machine for the manufacture of sanitary towels, the machine corresponding to the cutting machine whose schematic outline is given in FIG. 1.

Referring now to FIGS. 1 and 2, it will be seen that the cutting machine in accordance with the invention receives a continuous strip 1 which is to be cut into sections. Strip 1 is formed by a superposition of plastic sheets and fibrous layers and it is to be cut into sections intended to form discrete sanitary towels.

The strip 1 is advanced to a first cutter unit formed by a cylindrical cutter carrier 2 and a counter roller 3. The arbors of the cylindrical cutter carrier 2 and of the counter roller 3 are fixed, parallel and directly one above the other. The cutter of the cylindrical cutter carrier 2 has an edge 4 projecting from the cylindrical outer surface of cylinder 2, the entire cutter member being designated 5. The cutting edge 4 has a rounded shape whose convexity faces towards the left as viewed in FIGS. 1 and 2 (see FIG. 2). Strip 1 leaves its forming station (not shown) with a translatory motion along the arrow F of FIG. 2, that is to say from the right to left on FIGS. 1 and 2. Cutting edge 4 cuts the strip 1 along the edge 6 and thus cut section 7 is entrained by the first conveyor unit of the machine (to be described below).

The first conveyor unit of the machine comprises a rotary cam 8 bearing on the cut towel section 7 which is meanwhile supported by counter surface means in the form of a conveyor belt 9. The linear speed of belt 9 is the same as that of the cam surface 8a of the cam 8. This speed is higher than the displacement velocity of strip 1. Cam 8 is adjusted so that the cam surface 8a bears on section 7 when the cut has been effected by the cutting edge 4 of cutter 5. It follows that, as the cutting is effected, the section 7 becomes separated from the strip 1 and is conveyed, after passing under cam 8, between the belt 9 and a second belt 10. The belts 9 and 10 are for this purpose displaced at the same linear velocity. The endless belt 9 is carried on rollers 11, 12, 13 and 14 and the endless belt 10 on rollers 15 and 16. For each belt, there is a drive roller and at least one tension adjusting idler roller.

The cut section 7 is thus brought to the second cutter unit which comprises a cylindrical cutter carrier 17 and a counter roller generally designated 18. The cylindrical cutter carrier 17 is similar to the cylindrical cutter carrier 2, but the carrier 19 which it carries forms an edge whose convexity, at the time of cutting, is orientated in the opposite direction from the convexity of edge 4 at the moment when the cutting is effected in the first cutter unit. In other words, the cutting edge 20 of cutter 19 makes it possible to effect a cut edge whose convexity faces towards the right as viewed in FIGS. 1 and 2 (see particularly FIG. 2) so that during this second cut the cut section 7 is divided to form a recut section 7a and an off-cut 7b.

The off-cut 7b is located opposite one of two diametrically opposite inserted plates 21 fitted in the outer surface of the counter roller 18. The inserted plate 21 is traversed by suction channels 22 which are connected to a suction chamber 23 forming a sector of an annulus subtending with an angle $\theta$ which is at the center of the counter roller, the rest of the said annulus being designated by 24. The annulus portion 24 and the suction chamber sector 23 are fixed, whereas the outer surface of the counter roller 18 is formed by a sleeve 25 which is carried for rotation with the arbor 26 of the counter roller 18. The counter roller 18 comprises two diametrically opposite cutting zones embodied by the two inserted plates 21. The outer diameter of counter roller 18 is twice the diameter of the corresponding cylindrical cutting surface of the cylindrical cutter carrier 17.

When the second cut (along the edge 6a) has been effected by the cutter 19, the recut towel section 7a is seized by a rotary cam 27 of the second conveyor unit of the machine. The cam surface of this cam 27 has a higher linear velocity than that of the towel section 7. Therefore the recut towel section 7a moves away from off-cut 7b once the cut has been effected. Cam 27 bears on the top of towel section 7a meanwhile the said towel section rests on support surface means formed by a fixed counter plate 28 along which it slides. Towel section 7a thus arrives opposite another rotary cam 29 which increases its translational velocity still further. The action of cam 29 on towel section 7a is, however, only exerted once the cam surface of cam 27 has relaxed its action on the towel section 7a. When cam 29 bears on towel section 7a, the said section is supported by support surface means formed by a rotating counter roller 30. The set of elements 27, 28, 29 and 30 forms the second conveyor unit of the machine.

In FIG. 1, the directions of rotation of all the rotating elements of the machine have been indicated by arrows.

When the cut has been effected by the cutting edge 20 of cutter 19, the off-cut 7b is kept in contact with the inserted plate 21 of the counter roller 19. This is accomplished by reason of the suction through suction chanels 22. This suction is maintained over an angular sector $\theta$ in the rotation of counter roller 18, after which the channels 22 no longer communicate with the suction chamber 23. In this way the suction is suppressed and the off-cut 7b may be separated from the outer surface of sleeve 25 of the counter roller 18. However, to improve this separation provision may be made for a scraper device 31 to scrape the outer surface of the counter roller 18 and for a blowing device (not shown in the drawing) to direct an air jet onto the off-cut 7b below the suction cut-off location, i.e. just upstream of the scraper device 31. Off-cut 7b may thus detach itself from the outer surface of roller 18 and fall into a disposal chute 32 along arrow G under the influence of gravity.

Thus, the recut towel sections 7a which are dispensed at the machine outlet are separated from the off-cuts 7b which are ejected into a disposal chute.

FIGS. 3 to 8 show in greater detail the embodiment of the machine whose working principle is exemplified in FIG. 1.

Figure 4:
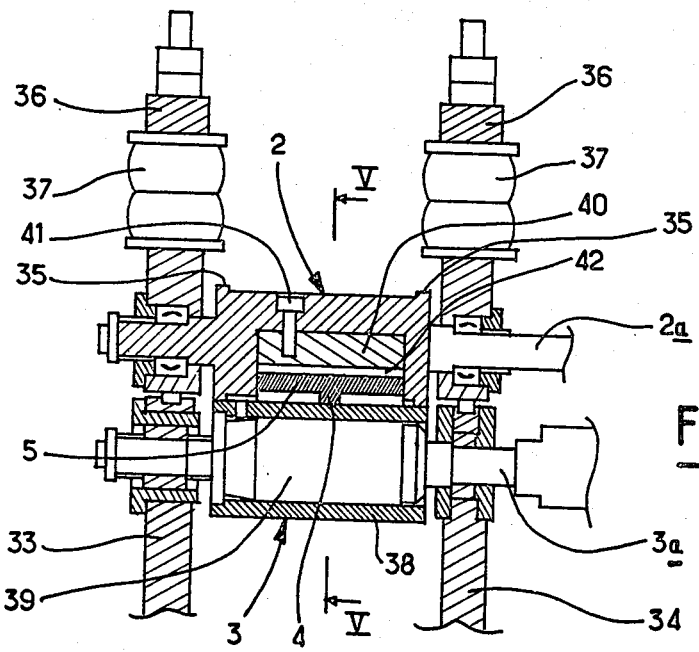
FIG. 4 is a partial cross-section, along the line IV—IV of FIG. 3, showing the elements forming the first cutter units.
Figure 5:
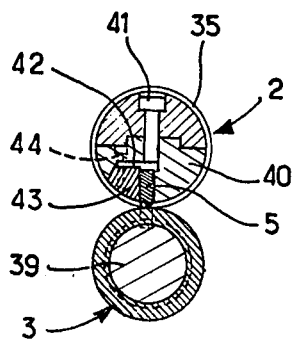
FIG. 5 is a cross-section taken along the line V—V of FIG. 4.
Figure 8:
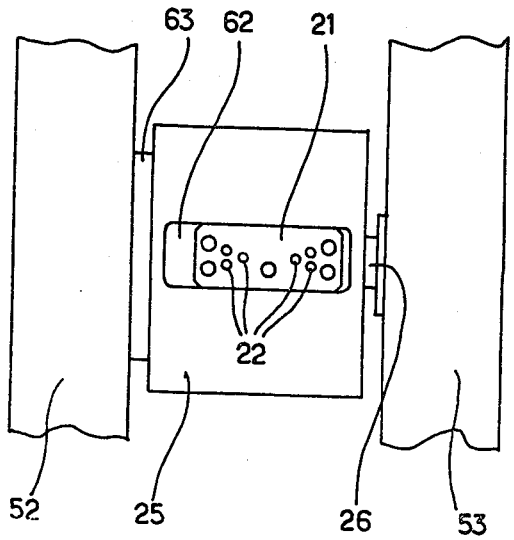
FIG. 8 is a detail section taken along the line VIII—VIII of FIG. 6.
Figure 7:
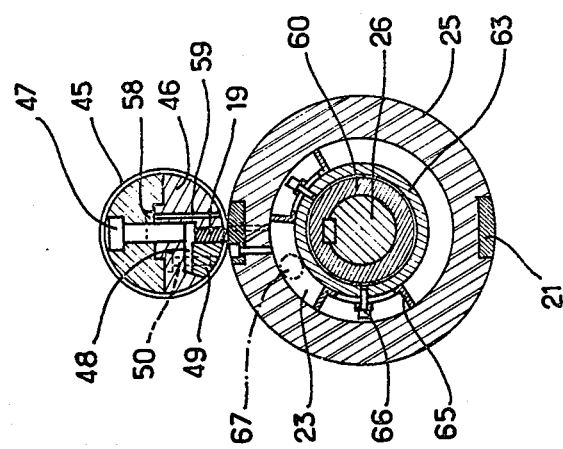
FIG. 7 is a cross-section taken along the line VII—VII of FIG. 6.
Figure 6:
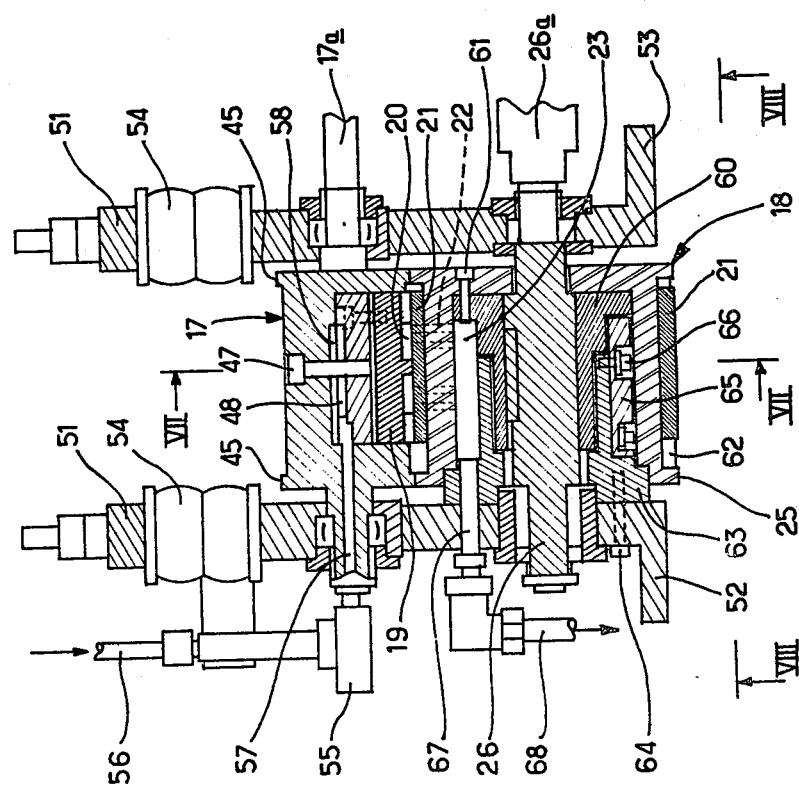
FIG. 6 is a partial cross-section of the elements forming the second cutter unit, taken along the line VI—VI of FIG. 3.

FIGS. 4 and 5 relates to the embodiment of the first cutter unit. It will be seen that the arbor 2a of the cylindrical cutter carrier 2 and that, 3a, of the counter roller 3 are carried by parallel side plates 33, 34 of the frame. These side plates 33, 34 are vertical and parallel to the displacement axis of strip 1 as it enters the cutting machine according to the invention. The drive of cylinder 2 and of counter roller 3 is effected by these arbors 2a and 3a respectively. Cylinder 2 rolls, without sliding, on counter roller 3. This is achieved by virtue of the cylinder flanges 35 which are situated at the two ends of cylinder 2 and which bear on the corresponding end zones of the cylindrical surface of the roller 3. The bearing action of cylinder 2 against counter roller 3 is maintained by fixing bars 36 screwed on to the side plates 33 and 34 of the frame with the interposition of an elastic mounting system formed by elastomer cylinders 37 which have been precompressed. Roller 3 is formed by a liner 38 which is fitted on a large diameter arbor 39. Cylinder 2 comprises, between the flanges 35, a hollow zone wherein there is arranged an inserted component 40 which is fixed to the cylinder 2 by means of fixing bolts 41. The inserted component 40 in turn comprises a cavity 42 to receive on the one hand the cutter 5 and on the other hand a setting wedge 43 which is tightened in the cavity 42 by means of a screw 44.

In the second cutting unit of the machine, the cylindrical cutter carrier 17 has a structure similar to that of the cylindrical cutter carrier 2. It rolls, without sliding, on the counter roller 18 due to the bearing action of the bearing flanges 45 on the outer surface of the sleeve 25 of counter roller 18. Cylinder 17 comprises, between flanges 45, an inserted component 46 fixed to the cylinder 17 proper by means of bolts 47. The inserted component 46 itself comprises a cavity 48 to receive a wedge 49 which allows the cutter 19 to be fixed by the tightening of the wedge by means of screw 50. The contact of cylinder 17 on counter roller 18 is achieved by virtue of bars 51 which keep the arbor of cylinder 17 in position in relation to side plates 52, 53 of the frame. The side plates 52 and 53 are similar to the side plates 33 and 34 described above, and support all the elements of the second cutting unit and of the second conveyor unit. The fixing of cylinder 17 on side plates 52 and 53 is effected with interposition of compressed elastomer cylinders 54 which are identical to the corresponding cylinders 37 of the first cutting unit.

The cylindrical cutter carrier 17 has a special feature differentiating it from the cylindrical cutter carrier 2, since it receives along its arbor a compressed air supply by means of a revolving joint 55 supplied via conduit 56. The compressed air is forwarded, via the axial channel 57, into a compartment 58 defined at the bottom of the cavity containing the inserted component 46. The inserted component 46 is traversed by air ducts 59 arranged substantially parallel to cutter 19 on the convex side of this cutter. In this way, the channels 59 open out onto the side surface of cylinder 17 ahead of cutting edge 20, that is to say, opposite the zone where off-cut 7b is produced. This precaution prevents the off-cut from remaining attached to the cylindrical cutter carrier 17.

The counter roller 18 turns in side plates 52 and 53 by means of its arbor 26, which is caused to rotate by its end 26a just as cylinder 17 is caused to rotate by its arbor 17a. Attached on arbor 26, there is a keyed collar 60 to which the sleeve 25, constituting the outer surface of counter roller 18, is fixed by means of bolts 61. In the two cutting zones which come to be opposite edge 20 of cutter 19, the sleeve 25 of the counter roller 18 comprises recesses 62 receiving the inserted plates 21. On collar 60 is a muff 63 which is fixed to the frame by means of bolts 64. Between muff 63 and the inner surface of sleeve 25, there is defined an annular space. In this annular space are two cylindrical sectors 65 which are fixed on the muff 63 by means of screws 66. The cylindrical sectors 65 delimit between them a zone extending over an angular sector $\theta$ of approximately 70°.

This zone forms the suction chamber 23 and is connected via ducting 67 to a suction conduit 68. The suction chamber 23 starts slightly ahead of the zone where the cutting due to edge 20 is effected. It extends over angle θ in the direction of rotation of the sleeve 25. The suction chamber 23 is connected to the cutting zone via the suction channels 22 which pass through the sleeve 25 and the inserted plates 21. In this way, the off-cuts 7b are kept in position on the surface of the counter roller 18.

It will be seen that the machine which has been described above makes it possible to make, out of a continuous strip moved in translation, a sequence of towel sections having cuts at their two ends which are convex towards the outside. This machine is reliable in operation and does not give rise to any jamming due to the off-cuts being retained in position in the zone of the cylindrical cutter carriers. All the off-cuts are evacuated by way of the off-cut chute, the cut towel sections leaving the machine interspaced from each other. Such a machine can attain a very high production rate. This machine is especially suitable for making sanitary towels with rounded ends.

It shall be duly understood that the embodiment described above is in no way restrictive, and may give rise to any desirable modifications without thereby departing from the scope of the invention as defined by the claims.

I claim:

1. A machine for cutting a continuous strip which is movable in horizontal translation,
said machine being adapted to form from the strip cut sections characterized in being bounded by rounded cut edges which opposite convexities, such machine comprising, in sequence, along the direction of translation of the strip:
(a) first rotary cutter means including:
(i) a first cylindrical cutter carrier;
(ii) a first cutter at the surface of said first cutter carrier, said first cutter having an edge which has a rounded outline;
(iii) a first counter roller rotatable so as to be tangential to the said cutter edge;
(iv) an arbor to said first cylindrical cutter carrier;
(v) an arbor to said first counter roller;
said arbors being fixed in position, parallel and arranged one above the other; and
(vi) means rotating said arbors in opposite directions to give the cutter edge and the counter roller a linear displacement velocity equal to that of the strip;
(b) first conveyor means operative to convey a strip section cut by said first rotary cutter means to impart a higher linear velocity than that of the strip when the cut has been effected;
(c) second rotary cutter means including:
(i) a second cylindrical cutter carrier;
(ii) a second cutter carried peripherally by said second carrier;
(iii) a second counter roller;
(vi) an arbor to said second cylindrical cutter carrier;
(v) an arbor to said second counter roller;
(vi) means effective to rotate said arbors in opposite directions to give the second cutter and the second counter roller a linear displacement velocity equal to that of the strip section being cut by said second rotary cutter means;

said second cutter forming an edge with a rounded outline whose convexity is, at the moment of cut, opposite to that of said first cutter of the first rotary cutter means;
said arbors of the second cylindrical cutter carrier and of the second counter roller being fixed in position, parallel and arranged one above the other;
the second counter roller being tangential to the cutting edge of said second cutter; and
(vii) suction means to said second counter roller effective to apply suction just ahead of the said cutter edge where said second cutter is tangent to said second counter roller in order to keep the off-cut on the second counter roller;
said suction means being arranged to cut off the application of suction after rotation of the counter roller and off-cut through a fraction of a revolution to allow the said off-cut to be removed from said second counter roller; and
(d) second conveyor means imparting a linear velocity to the cut section leaving
said second rotary cutting means higher than that of the cut section arriving at said second rotary cutting means.

2. A machine according to claim 1, wherein:
said second counter roller includes
means defining a fixed suction chamber internally thereof forming a sector of an annulus subtending at the center of said second counter roller which is less than 360°;
a sleeve forming the outer cylindrical surface of said second counter roller rotating around said annulus; and
suction conduits passing through the said sleeve in the zones which are just ahead of the edge of the said second cutter at a position where said edge is to be tangent to the outer surface of the sleeve at the instant of cutting.

3. A machine according to claim 2, and including in additional combination therewith:
means, adjacent the counter roller of the second cutter means, defining a recovery chute for receiving the off-cuts from the second cutter,
said recovery chute being displaced around the axis of the second counter roller from the zone of the second cut by a second angle greater than said first angle.

4. A machine according to claim 3, wherein:
the recovery chute is adapted to effect the recovery of the off-cuts by means of gravity, and including and in additional combination therewith
at least one of:
(e) scraper means bearing on the outer surface of the second cutter roller; and
(f) blowing means detaching the off-cuts from the second counter roller.

5. A machine according to claim 2, wherein:
the outer diameter of said sleeve of the second counter roller is twice the diameter of a cylindrical surface swept by the radially outer part of the edge of the second cutter; and
said swept surface has its axis coaxial with the axis of the second cylindrical cutter carrier;
and also wherein the above-mentioned sleeve has diametrically opposite inserted plates defining two cutting zones and comprising at least a part of said suction conduits.

6. A machine according to any one of claims 1 to 5, wherein:
   the said second cutter is a component which is inserted into said first cutter carrier; and
   said second cutter is a component which is inserted into the said second cylindrical cutter carrier.

7. A machine according to any one of claims 1 to 5, wherein:
   the first and second cylindrical cutter carriers include means bearing on the respective one of said first and second counter rollers and which roll thereon without sliding; and including and in additional combination therewith
   resilient means maintaining the contact of the said first and second cylindrical cutter carriers on the said respective counter rollers.

8. A machine according to any one of claims 1 to 5, wherein:
   said second cylindrical cutter carrier includes means defining blowing ducts opening outwardly and just behind the second cutter edge during cutting.

9. A machine that is in accordance with any one of those of claims 1, 2, 3, 4 or 5, inclusive, and including in addition thereto and combination therewith:
   means for feeding to and physically passing through said machine at least substantially flat strips of material stock to be further fabricated by said machine,
   which stock is comprised of combined layer of flat goods selected from the Group consisting of textile materials, fiber products, mixtures thereof and combined layers of adjacently-contiguous plastic sheets or films additionally covering and associated with one or more of said textile materials and said fiber products, as well as mixtures of said additionally-sheet-or-film covered flat goods; with
   said cutter means being adapted to cut out as scrap from said flat strips of material stock being fabricated sections therefrom having a bi-concave shape; and
   said cutter means in said machine being further adapted to cut said flat strips of material stock fed to and passed through said machine into fabricated product in a form and shape suitable for application and use as feminine sanitary towels or napkins that have been cut from said material stock upon and after passage through and exit delivery from the said machine.

10. A machine according to any one of claims 1 to 5, wherein:
    each of said first and second conveyor means comprises:
    (g) rotary cam means which bear on the cut section which has just been subjected to a cut,
    said cam means being driven relative to the rest of the respective conveyor means such that contact of the cam means with the cut section increases its linear velocity; and
    (h) counter surface means for carrying the said section being driven by contact with said cam means.

11. A machine according to claim 10, wherein:
    said counter surface means is a belt driven at the linear velocity which is intended to be imparted to the cut section contacted by said cam means.

12. A machine according to claim 10, wherein:
    said counter surface means is a fixed plate on which the conveyed cut section slides.

13. A machine according to claim 10, wherein:
    said counter surface means is a roller driven at the liner velocity of the cam surface of said cam means with which it cooperates.

14. The machine of claim 10, and including
    in further addition thereto and combination therewith:
    (x) additional rotary cam means in said second conveyor means (d) having a cam surface with a higher linear velocity than that of said cut section and which bears on the surface of the cut section ahead of said rotary cam means (g) in the said second conveyor means (d) during the time that said cut section is passing therethrough, so that
    the movement of said cut section is assured through said second conveyor means (d) in such a way as to obtain a constant length of said off-cut between successive cut sections passing therethrough; with
    said additional rotary cam means (x) being adapted to drop each of said cut sections whenever said second conveyor means (d) is activated in order to extricate a given cut section.

15. The machine of claim 1, and including
    in further addition thereto and combination therewith:
    (x) additional conveyor means in said second conveyor means (d) having a cam surface with a higher linear velocity than that of the cut section and which bears on the surface of the cut section at the beginning entry for said cut sections into said second conveyor means (d) immediately after said cut sections leave said second rotary cutter means (c) during the time that said cut section is passing therethrough; so that
    the movement of said cut section is assured through said second conveyor means (d) in such a way as to obtain a constant length of said off-cut between successive cut sections passing therethrough; with
    said additional rotary cam means (x) being adapted to drop each of said cut sections whenever said second conveyor means (d) is activated in order to extricate a given cut section.

* * * * *